United States Patent
Marshall et al.

(10) Patent No.: US 11,684,436 B2
(45) Date of Patent: *Jun. 27, 2023

(54) SURGICAL ROBOT DRIVING MECHANISM

(71) Applicant: CMR Surgical Limited, Cambridge (GB)

(72) Inventors: Keith Marshall, Cambridge (GB); Steven James Randle, Stratford-upon-Avon (GB)

(73) Assignee: CMR Surgical Limited, Cambridge (GB)

( * ) Notice: Subject to any disclaimer, the term of this patent is extended or adjusted under 35 U.S.C. 154(b) by 403 days.

This patent is subject to a terminal disclaimer.

(21) Appl. No.: 16/909,012

(22) Filed: Jun. 23, 2020

(65) Prior Publication Data

US 2020/0315719 A1    Oct. 8, 2020

Related U.S. Application Data

(63) Continuation of application No. 15/576,551, filed as application No. PCT/GB2016/051469 on May 20, 2016, now Pat. No. 10,722,312.

(30) Foreign Application Priority Data

May 22, 2015    (GB) ..................... 1508813

(51) Int. Cl.
    *A61B 34/30*    (2016.01)
    *A61B 34/00*    (2016.01)
(52) U.S. Cl.
    CPC .............. *A61B 34/30* (2016.02); *A61B 34/71* (2016.02); *A61B 2034/305* (2016.02)
(58) Field of Classification Search
    CPC ......... A61B 34/30; A61B 34/37; A61B 34/70; A61B 34/71; A61B 34/77; A61B 2034/305

See application file for complete search history.

(56) References Cited

U.S. PATENT DOCUMENTS

2004/0266574 A1* 12/2004 Jinno ..................... A61B 34/71
                                                474/174
2008/0039892 A1    2/2008 Mitsuishi et al.
(Continued)

FOREIGN PATENT DOCUMENTS

EP        2869779 B1    5/2015
WO    2011016640 A2    2/2011
(Continued)

OTHER PUBLICATIONS

GB Search Report for GB Application No. 1508813.1 dated Dec. 4, 2015, 1 page.
(Continued)

*Primary Examiner* — Tuan V Nguyen
(74) *Attorney, Agent, or Firm* — Finch & Maloney PLLC (57) ABSTRACT

A surgical robot comprising a surgical robot arm and a surgical instrument. The surgical robot arm terminates at its distal end in a drive assembly comprising a first drive interface element. The surgical instrument comprises a shaft, an articulation attached to the distal end of the shaft, and a driving mechanism at the proximal end of the shaft. The articulation is for articulating an end effector, the articulation driveable by at least a first driving element and a second driving element. The driving mechanism comprises a first instrument interface element to which the first driving element is connected and a second instrument interface element to which the second driving element is connected. The first drive interface element engages both the first and second instrument interface elements such that: when the first drive interface element moves linearly, both the first and second instrument interface elements move in the same linear direction thereby driving both the first and second driving elements in the same direction; and when the first drive interface element rotates, the first and second instrument interface elements move reciprocally in opposing (Continued)

linear directions thereby driving the first and second driving elements in opposing directions.

12 Claims, 9 Drawing Sheets

(56) References Cited

U.S. PATENT DOCUMENTS

| | | |
|---|---|---|
| 2014/0005681 A1 | 1/2014 | Gee |
| 2014/0128849 A1* | 5/2014 | Au .................. A61B 34/71 606/1 |
| 2014/0228861 A1 | 8/2014 | Kishi |
| 2018/0147017 A1 | 5/2018 | Marshall et al. |

FOREIGN PATENT DOCUMENTS

| | | |
|---|---|---|
| WO | 2013062132 A1 | 5/2013 |
| WO | 2014005689 A3 | 1/2014 |

OTHER PUBLICATIONS

International Search Report and Written Opinion received for PCT Application No. PCT/GB2016/051469 dated Nov. 8, 2016.
International Preliminary Report on Patentability received for PCT Application No. PCT/GB2016/051469, dated Nov. 28, 2017. 9 pages.

\* cited by examiner

SURGICAL ROBOT DRIVING MECHANISM

RELATED APPLICATIONS

This application claims priority to U.S. application Ser. No. 15/576,551, filed Nov. 22, 2017, which claims priority under 35 U.S.C. § 371 as a national stage application of PCT Application No. PCT/GB2016/051469, filed May 20, 2016, which claims priority to GB 1508813.1, filed May 22, 2015, each of which is hereby incorporated herein by reference in its entirety.

BACKGROUND

It is known to use robots for assisting and performing surgery. Surgical robots normally consist of a base, an arm, and an instrument. The base supports the robot, and is itself attached rigidly to, for example, the operating theatre floor, the operating theatre ceiling or a trolley. The arm extends between the base and the instrument. The arm typically has a plurality of articulations, which are used to locate the surgical instrument in a desired location relative to the patient. The surgical instrument is attached to the distal end of the robot arm. The surgical instrument penetrates the body of the patient at a port so as to access the surgical site.

Figure 1:
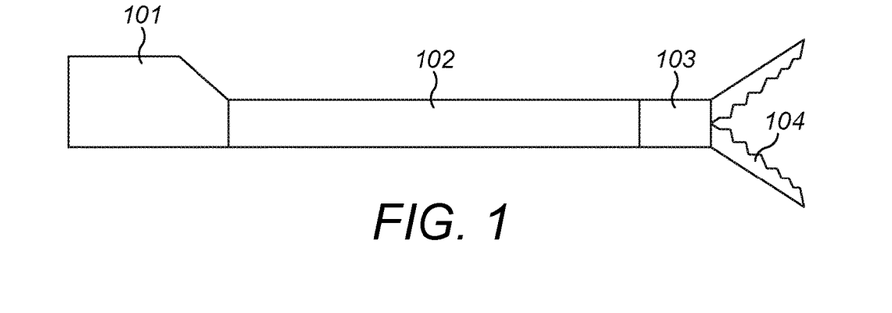
FIG. 1 illustrates a known surgical instrument.

FIG. 1 illustrates a typical surgical instrument 100 for performing robotic laparoscopic surgery. The surgical instrument comprises a base 101 by which the surgical instrument connects to the robot arm. A shaft 102 extends between base 101 and articulation 103. Articulation 103 terminates in an end effector 104. In FIG. 1, a pair of serrated jaws are illustrated as the end effector 104. The articulation 103 permits the end effector 104 to move relative to the shaft 102. It is desirable for at least two degrees of freedom to be provided to the motion of the end effector 104 by means of the articulation.

Figure 2:
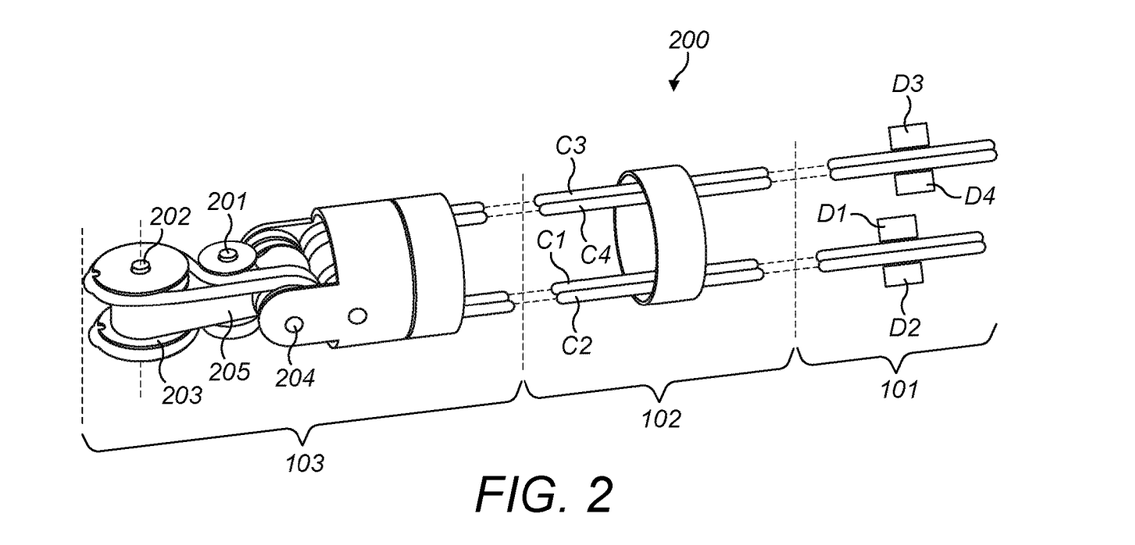
FIG. 2 illustrates a known cabling arrangement of a surgical instrument.

FIG. 2 illustrates an example of a known cabling arrangement 200 in a surgical instrument for transferring drive from the base of the surgical instrument 101 through the shaft 102 to the articulation 103. Cable pair C1, C2 terminate in the articulation as a loop around capstan 202. They then pass as a pair around one side of capstan 201. From there, the cable pair C1, C2 passes over capstan 204 and down through shaft 102 to the base of the instrument 101. Cable pair C3, C4 terminate in the articulation as a loop around capstan 203. They then pass as a pair around the other side of capstan 201 to C1, C2. From there, the cable pair C3, C4 passes under capstan 204 and down through shaft 102 to the base of the instrument 101.

Rotation of yoke 205 about capstan 204 causes the articulation 103 and hence the end effector 104 to pitch about the capstan 204. Pitching in one direction is enabled by pulling cable pair C1, C2 and releasing cable pair C3, C4. Pitching in the other direction is enabled by pulling cable pair C3, C4 and releasing cable pair C1, C2. Rotation of capstan 202 causes one jaw of end effector 104 to move. Movement in one direction is enabled by pulling cable C1 and releasing cable C2. Movement in the other direction is enabled by pulling cable C2 and releasing cable C1. Rotation of capstan 203 causes the other jaw of end effector 104 to move. Movement in one direction is enabled by pulling cable C3 and releasing cable C4. Movement in the other direction is enabled by pulling cable C4 and releasing cable C3.

Figure 3:
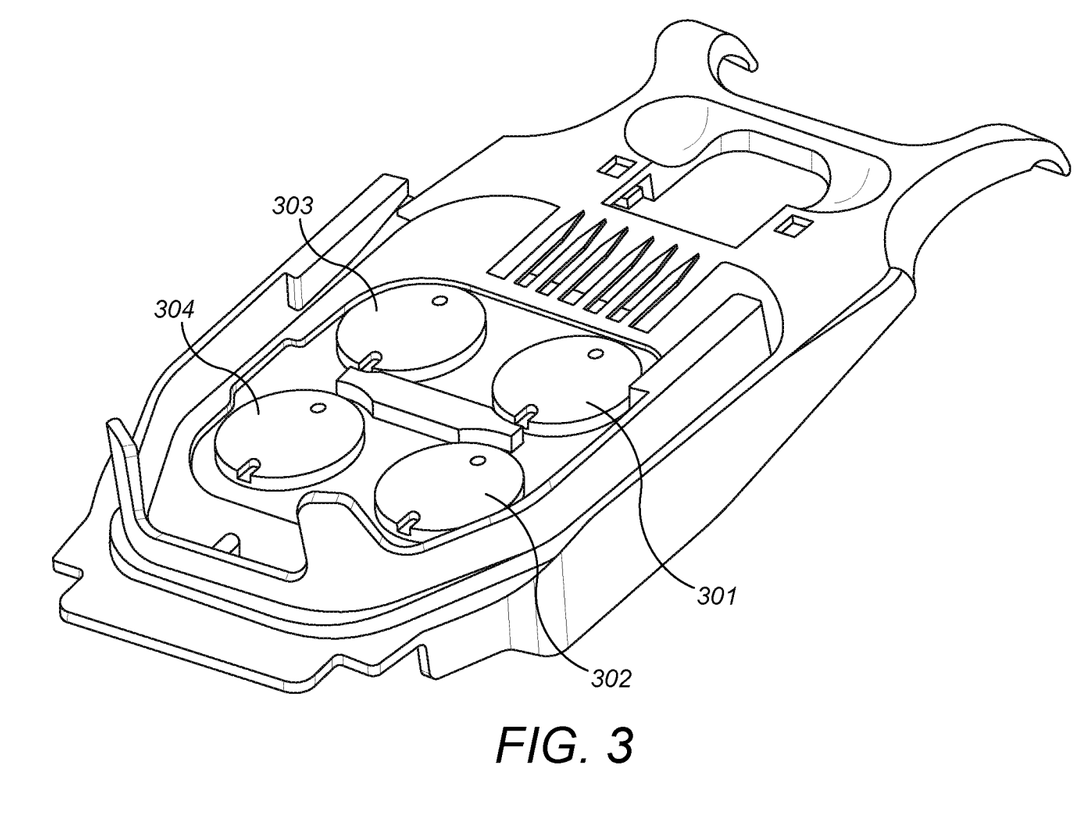
FIG. 3 illustrates a known interface plate for interfacing a surgical robot arm and a surgical instrument.

Cables C1, C2, C3 and C4 are driven individually and independently by drivers D1, D2, D3 and D4 respectively. These drivers are typically located in the robot arm, and their drive is transmitted to the surgical instrument via an interface between the robot arm and the surgical instrument. A known interface plate is shown in FIG. 3. Spools 301, 302, 303 and 304 are used to transfer the drive from the robot arm to the surgical instrument. Drivers D1, D2, D3 and D4 in the robot arm provide drive to four cables in the robot arm which terminate at complimentary spool features to the spools 301, 302, 303 and 304. These complimentary spool features lock on to the spools 301, 302, 303, 304 such that a rotation of a complimentary spool feature causes a corresponding rotation of the spool to which it is locked. On the opposite side of the interface place, cables C1, C2, C3 and C4 terminate at complimentary spool features to the spools 301, 302, 303 and 304. The complimentary spool features lock onto the opposite sides of spools 301, 302, 303 and 304 such that a rotation of a spool causes a corresponding rotation of the complimentary spool feature to which it is locked. Thus, drive is transferred from drivers D1, D2, D3 and D4 to cables C1, C2, C3 and C4.

The interfacing arrangement illustrated in FIG. 3 is complex, and requires many precisely made components, which need to be aligned and locked together accurately in the operating theatre. Every time an instrument is replaced during an operation, the instrument must be detached from the interface plate, and another instrument accurately aligned and locked into the interface plate in order to enable the instrument to be used.

SUMMARY OF THE INVENTION

According to an aspect of the invention, there is provided a surgical robot arm terminating at its distal end in a drive assembly for driving a surgical instrument, the surgical instrument having an articulation for articulating an end effector, the articulation driveable by at least a first driving element and a second driving element, the drive assembly comprising: a first drive interface element configured to engage with a first instrument interface element for coupling drive to the first driving element and a second instrument interface element for coupling drive to the second driving element, wherein the first drive interface element is permitted to: move linearly so as to cause the first and second instrument interface elements to move in the same direction thereby driving both the first and second driving elements in the same direction; and rotate so as to cause reciprocal motion of the first and second instrument interface elements in opposing directions thereby driving the first and second driving elements in opposing directions.

Suitably, the first drive interface element is permitted to rotate about an axis disposed halfway between where the first drive interface element engages with the first instrument interface element and where the first drive interface element engages with the second instrument interface element, such that rotation of the first drive interface element causes linear motion of the first instrument interface element in one direction and a matching linear motion of the second instrument interface element in an opposing direction.

The first drive interface element may be permitted to move linearly along a longitudinal axis of the proximal end of the shaft.

Suitably, the first drive interface element is permitted to rotate about an axis perpendicular to a longitudinal axis of the proximal end of the shaft.

The first drive interface element may be rigid.

The first drive interface element may comprise two arms configured to embrace the first and second instrument interface elements.

The first drive interface element may be U-shaped.

The drive assembly may further comprise a second drive interface element configured to engage with a third instrument interface element for coupling drive to a third driving element and a fourth instrument interface element for coupling drive to a fourth driving element, wherein the second drive interface element is permitted to: move linearly so as to cause the third and fourth instrument interface elements to move in the same direction thereby driving both the third and fourth driving elements in the same direction; and rotate so as to cause reciprocal motion of the third and fourth instrument interface elements in opposing directions thereby driving the third and fourth driving elements in opposing directions.

The drive assembly may be configured to move the first drive interface element and the second drive interface element independently of each other.

According to a second aspect of the invention, there is provided a robotic surgical instrument comprising: a shaft; an articulation attached to the distal end of the shaft, the articulation for articulating an end effector, the articulation driveable by at least a first driving element and a second driving element; and a driving mechanism at the proximal end of the shaft, the driving mechanism comprising: a first slideable unit to which the first driving element is secured, and a second slideable unit to which the second driving element is secured, wherein the first and second slideable units are permitted to slide linearly relative to each other; a first instrument interface element connected to the first slideable unit, and a second instrument interface element connected to the second slideable unit, both the first and second instrument interface elements configured to engage with a first drive interface element of a drive assembly such that the first and second instrument interface elements are driveable in the same linear direction so as to drive both the first and second driving elements in the same direction, and the first and second instrument interface elements are driveable in opposing linear directions so as to drive the first and second driving elements in opposing directions.

The first and second slideable units may be stacked such that their longitudinal axes are parallel, and the first and second slideable units are permitted to slide parallel to their longitudinal axes.

The first instrument interface element may be a first rod protruding from the first slideable unit in a direction transverse to the longitudinal axis of the first slideable unit, and the second instrument interface element may be a second rod protruding from the second slideable unit in a direction transverse to the longitudinal axis of the second slideable unit.

The first and second rods may be parallel.

Suitably, in a configuration in which the articulation is de-tensioned, the first and second rods are aligned along an axis transverse to the longitudinal axes of the first and second slideable units and transverse to the longitudinal axes of the first and second rods.

The first and second rods may each be encompassed in a foam roller, each foam roller configured to engage with the first drive interface element.

Suitably, the articulation is additionally driveable by a third driving element and a fourth driving element; and wherein the driving mechanism further comprises: a third slideable unit to which the third driving element is secured, and a fourth slideable unit to which the fourth driving element is secured, wherein the first, second, third and fourth slideable units are permitted to slide linearly relative to each other; a third instrument interface element connected to the third slideable unit, and a fourth instrument interface element connected to the fourth slideable unit, both the third and fourth instrument interface elements configured to engage with a second drive interface element of the drive assembly such that the third and fourth instrument interface elements are driveable in the same linear direction so as to drive both the third and fourth driving elements in the same direction, and the third and fourth instrument interface elements are driveable in opposing linear directions so as to drive the third and fourth and elements in opposing directions.

Suitably, the first, second, third and fourth slideable units are stacked such that their longitudinal axes are parallel, and the first, second, third and fourth slideable units are permitted to slide relative to each other parallel to their longitudinal axes. The first, second, third and fourth slideable units may be stacked in a 2×2 configuration, such that the first and second instrument interface elements are on an opposing face of the configuration as the third and fourth instrument interface elements.

Suitably, the articulation is a wrist articulation comprising a pitch joint which is configured to pitch the wrist articulation, the first, second, third and fourth driving elements being connected to the wrist articulation such that: when the first and second slideable units are displaced linearly in a first direction by the first drive interface element, and the third and fourth slideable units are displaced linearly in the opposing direction by the second drive interface element, the wrist articulation pitches in one direction about the pitch joint; and when the first and second slideable units are displaced linearly in the opposing direction by the first drive interface element, and the third and fourth slideable units are displaced linearly in the first direction by the second drive interface element, the wrist articulation pitches in the opposing direction about the pitch joint.

Suitably, the articulation comprises a joint configured to actuate opposing first and second jaws of an end effector, the first and second driving elements being connected to the joint such that when the first and second slideable units are displaced linearly in opposing directions by the first drive interface element, the first jaw rotates in one direction about the joint, and when the first drive interface element applies a drive in an opposing direction the first jaw rotates in an opposing direction about that joint.

The third and fourth driving elements may be connected to the joint such that when the third and fourth slideable units are displaced linearly in opposing directions by the second drive interface element, the second jaw rotates in one direction about the joint, and when the second drive interface element applies a drive in an opposing direction the second jaw rotates in an opposing direction about that joint.

The driving elements may be elongate and flexible. The driving elements may be cables. The driving elements may resist compression and tension forces.

According to a third aspect of the invention, there is provided a surgical robot comprising: a surgical robot arm terminating at its distal end in a drive assembly, the drive assembly comprising a first drive interface element; and a surgical instrument comprising: a shaft; an articulation attached to the distal end of the shaft, the articulation for articulating an end effector, the articulation driveable by at least a first driving element and a second driving element; and a driving mechanism at the proximal end of the shaft, the driving mechanism comprising a first instrument interface element to which the first driving element is connected and a second instrument interface element to which the second driving element is connected; wherein the first drive interface element engages both the first and second instrument interface elements such that: when the first drive interface element moves linearly, both the first and second instrument interface elements move in the same linear direction thereby driving both the first and second driving elements in the same direction; and when the first drive interface element rotates, the first and second instrument interface elements move reciprocally in opposing linear directions thereby driving the first and second driving elements in opposing directions.

A covering may be disposed over the driving mechanism so as to provide a sterile barrier between the instrument interface elements and the drive interface elements.

BRIEF DESCRIPTION OF THE FIGURES

The present invention will now be described by way of example with reference to the accompanying drawings. In the drawings.

DETAILED DESCRIPTION

Figure 4A:
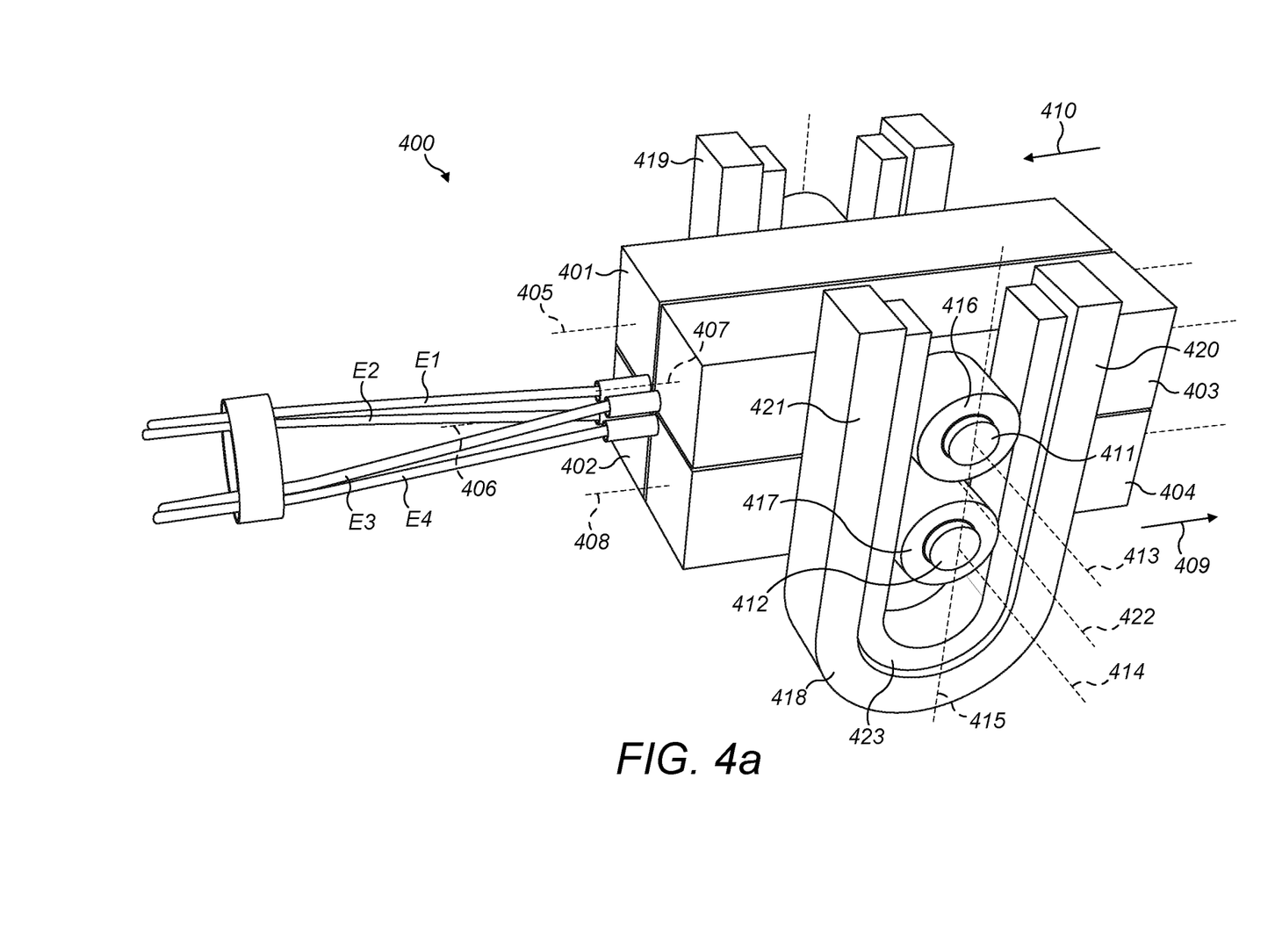
FIGS. 4a, 4b and 4c illustrate a driving mechanism at the end of the surgical instrument distal from the end effector and an interface of that driving mechanism with a drive assembly of the robot arm.

FIG. 4a illustrates a schematic drawing of an exemplary driving mechanism 400 of the interior of a robotic surgical instrument at the end of the surgical instrument distal from the end effector, and the interface of this driving mechanism with the drive assembly of a surgical robot arm. The surgical instrument as a whole has the general form shown in FIG. 1. In other words, the surgical instrument comprises a base 101 by which the surgical instrument connects to the surgical robot arm. The instrument base is designed cooperatively with the terminal end of the surgical robot arm, such that the instrument base is releasably attachable to the terminal end of the robot arm. A shaft 102 extends between the base 101 and an articulation 103. The articulation 103 is connected at its proximal end to the shaft 102 and at its distal end to an attachment suitable for attaching an end effector 104. The shaft 102 and articulation 103 are all hollow. This allows passage of elements up these sections to actuate the end effector 104. It also reduces the weight of the surgical instrument.

The end effector may take any suitable form. For example, the end effector may be smooth jaws, serrated jaws, a gripper, a pair of shears, a needle for suturing, a camera, a laser, a knife, a stapler, a cauteriser, a suctioner.

The driving mechanism of FIG. 4a is arranged to drive two pairs of driving elements, E1, E2 and E3, E4. The driving elements may, for example, be cables.

The driving mechanism of FIG. 4a comprises a set of slideable units. Driving element E1 terminates in slideable unit 401, driving element E2 terminates in slideable unit 402, driving element E3 terminates in slideable unit 403, and driving element E4 terminates in slideable unit 404. Each driving element is secured to the end of its slideable unit which is closest to the distal end of the shaft at which the articulation and end effector are located.

In FIG. 4a, the slideable units are blocks which are stacked such that their longitudinal axes 405, 406, 407 and 408 are parallel. The slideable units are permitted to slide linearly relative to each other. Suitably, the slideable units are permitted to slide parallel to their longitudinal axes. In FIG. 4a, the slideable units are depicted as each having a cuboid shape. Suitably, the slideable units have matching shapes and sizes. It will be understood that the slideable units may have any suitable shape that enables them to slide linearly relative to each other. The first and second slideable units 401 and 402 are stacked such that at least one side of slideable unit 401 is flush with one side of slideable unit 402. Similarly, the third and fourth slideable units 103 and 404 are stacked such that at least one side of slideable unit 403 is flush with one side of slideable unit 404. FIG. 4a illustrates slideable units 401 and 402 to be stacked on top of each other, and slideable units 403 and 404 to be stacked on top of each other, and slideable unit pair 401, 402 to be stacked side-by-side with slideable unit pair 403, 404 so as to form a 2×2 configuration in which longitudinal faces of the units are facing each other. Alternatively, the 2×2 configuration may be such that the short faces of slideable unit pair 401, 402 are facing the short faces of slideable unit pair 403, 404.

The longitudinal axes of the slideable units 405, 406, 407 and 408 are parallel to the longitudinal axes of the driving elements to which they are attached. Thus, linear movement of a slideable unit along its longitudinal axis causes the driving element to which it is connected to be tensioned or compressed along the longitudinal axis of the driving element. Suitably, both the longitudinal axes of the slideable units and the longitudinal axes of the driving elements are parallel to the longitudinal axis of the instrument shaft.

Figure 4B:
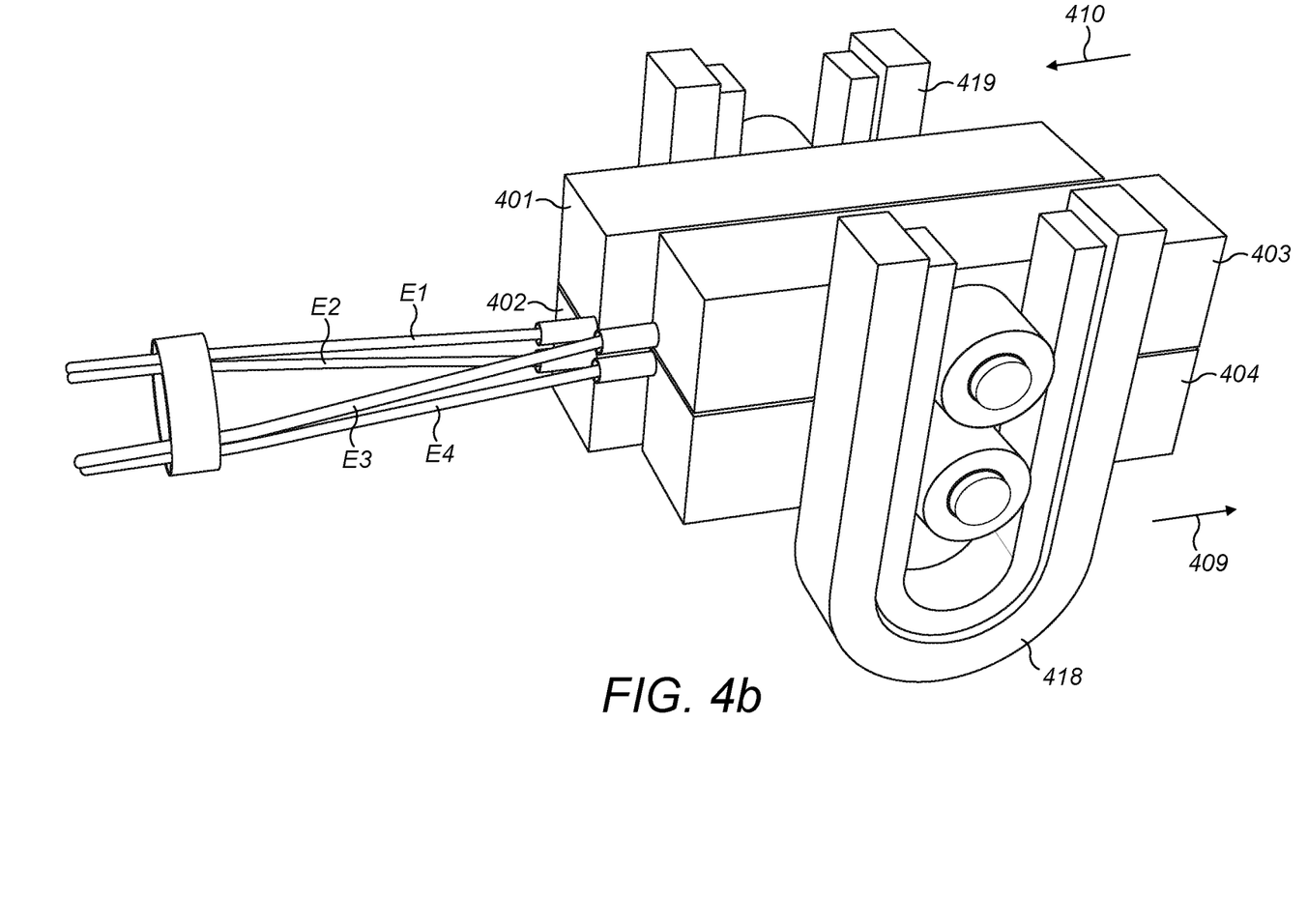

Each slideable unit of a slideable unit pair is permitted to move linearly in the same direction as the other slideable unit of the slideable unit pair. For example, FIG. 4b illustrates a configuration in which both slideable units 403 and 404 have moved in the direction of the arrow marked 409, and both slideable units 401, 402 have moved in the opposite direction, i.e. in the direction of the arrow marked 410. This thereby causes driving elements E3 and E4 to be tensioned, and driving elements E1 and E2 to be relaxed or compressed.

Figure 4C:
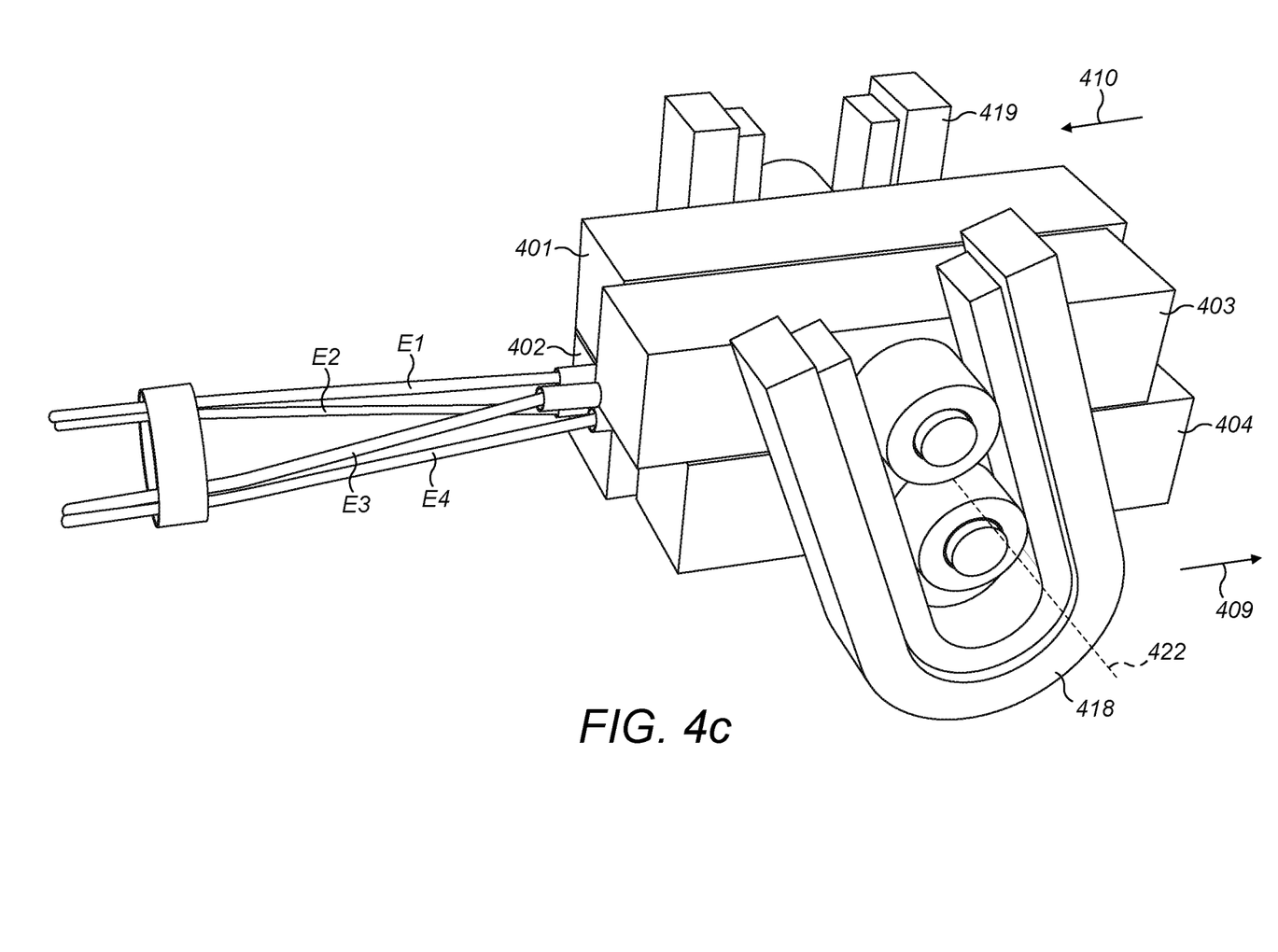

Each slideable unit of a slideable unit pair is permitted to move linearly in an opposing direction as the other slideable unit of the slideable unit pair. For example, FIG. 4c illustrates a configuration in which slideable unit 404 has moved in the direction of the arrow marked 409, and slideable unit 403 has moved in the opposite direction, i.e. in the direction of the arrow marked 410. This thereby causes driving element E4 to be tensioned, and driving element E3 to be relaxed or compressed.

An instrument interface element is connected to each slideable unit. The instrument interface element is configured to engage with a complimentary interface component of the robot arm, so as to enable the robot arm to selectively move the slideable units linearly, and thereby couple drive to the driving elements.

In FIG. 4a, each interface element is a rod 411, 412 protruding from the slideable unit. The rod is rigidly attached to the slideable unit. Thus, movement of the rod causes the slideable unit to move. The rod protrudes from the slideable unit in a direction transverse to the longitudinal axis of the slideable unit. The longitudinal axis of the rod 413, 414 is perpendicular to the longitudinal axis of the slideable unit 407, 408. The two rods which protrude from the slideable unit pair 401, 402 are parallel. The two rods which protrude from the slideable unit pair 403, 404 are parallel. Suitably, the rods protruding from all the slideable units are parallel to each other. In the example of FIG. 4*a*, the rods protruding from the slideable unit pair 401, 402 are on the opposing face of the 2×2 configuration than the rods protruding from the slideable unit pair 403, 404.

FIG. 4*a* illustrates a configuration of the driving mechanism in which the driving elements are at rest. In other words, none of the driving elements is being tensioned in the configuration of FIG. 4*a*. In this configuration, the centres of rod 411 of slideable unit 403 and rod 412 of slideable unit 404 are aligned along an axis 415 transverse to the longitudinal axes of the slideable units 403 and 404 and transverse to the longitudinal axes 413 and 414 of the rods 411 and 412. The rods of slideable units 401 and 402 are correspondingly aligned.

In the example of FIG. 4*a*, each rod is encompassed by a foam roller 416, 417. The foam roller engages with the interface element of the robot arm.

The drive assembly of the robot arm interfaces with the driving mechanism of the instrument via drive interface elements 418, 419. Drive interface element 418 engages the instrument interface elements of slideable units 403 and 404. Drive interface element 419 engages the instrument interface elements of slideable units 401 and 402. Drive interface element 419 acts on the slideable units 401 and 402 in the same way that drive interface element 418 acts on the slideable units 403 and 404. Thus, only drive interface element 418 is described in the following, and that description understood to apply correspondingly to drive interface element 419.

Drive interface element 418 engages both instrument interface element 411 of slideable unit 403 and the instrument interface element 412 of slideable unit 404. The drive interface element 418 in the example of FIG. 4*a* is a rigid, U-shaped structure. The arms 420 and 421 of the structure embrace both the rod 411 and the rod 412 equally in FIG. 4*a*. Each arm 420, 421 is in contact with both the instrument interface elements 411, 412.

The drive interface element 418 is permitted to move linearly along the longitudinal axes 407, 408 of the slideable units 403, 404. Such movement is illustrated in FIG. 4*b*. The whole of the drive interface element 418 has been displaced linearly in the direction 409 relative to FIG. 4*a*. The embrace of drive interface element 418 around the instrument interface elements is tight, thus movement of the drive interface element 418 causes movement of the instrument interface elements and hence the slideable units 403, 404. When the drive interface element 418 is displaced linearly in the direction 409, both of the slideable units 403, 404 are also both linearly displaced in the direction 409. The slideable units 403, 404 are both subject to the same displacement. This causes driving elements E3 and E4, which are rigidly secured to slideable units 403, 404, to be tensioned.

The drive interface element 418 is permitted to rotate about an axis 422. Axis 422 is perpendicular to the longitudinal axes 407 and 408 of slideable units 403 and 404. Axis 422 is parallel to the longitudinal axes 413, 414 of the rods 411, 412 and intersects the line between the centres of the rods 411, 412 halfway between the centres of the rods 411, 412. FIG. 4*c* illustrates an anticlockwise rotation of the drive interface element 418 about its rotation axis 413 relative to FIG. 4*a*. This rotation has caused slideable unit 403 to move in the linear direction 410 and slideable unit 404 to move in the linear direction 409. The motion of slideable unit 403 is reciprocal to the motion of slideable unit 404. Slideable unit 404 has been displaced in the linear direction 409 by the same amount that slideable unit 403 has been displaced in the opposing linear direction 410. This causes driving element E3 to be tensioned by the same magnitude that driving element E4 is compressed.

The drive assembly is configured to move the drive interface element 418 independently of the drive interface element 419. In FIG. 4*c*, the drive interface element 418 has been rotated about its axis whilst the drive interface element 419 has not been moved. In FIG. 4*b*, the drive interface element 418 has been driven in an opposing linear direction to the drive interface element 419.

Figure 5:
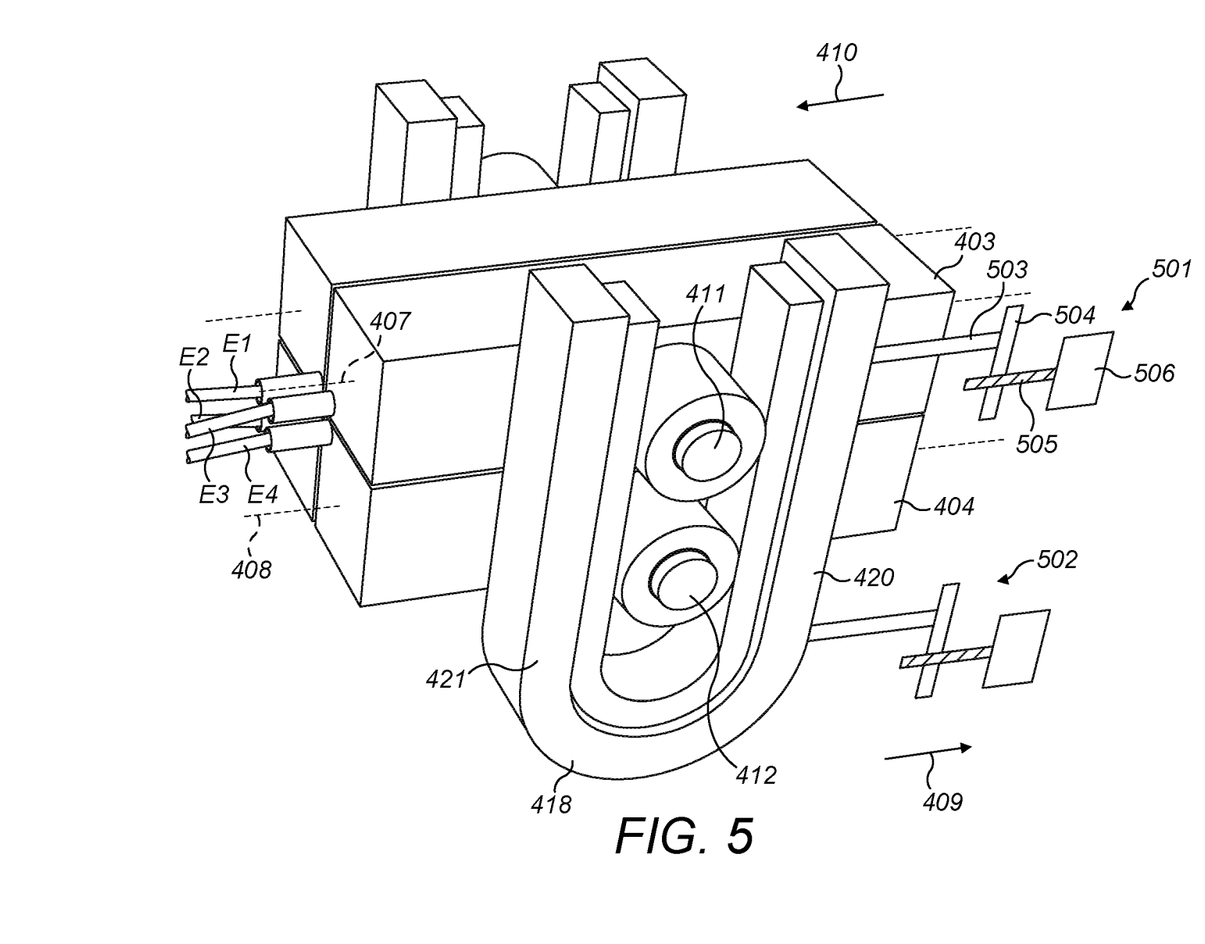
FIG. 5 illustrates an exemplary mechanism for coupling drive to the drive interface elements of the drive assembly of FIGS. 4a, 4b and 4c.

Any suitable mechanism may be used to drive interface element 418 in the manner described above. FIG. 5 illustrates an exemplary driving mechanism utilising two motor and lead screw arrangements. The first motor and lead screw arrangement 501 is attached to the drive interface element to one side of where the drive interface element embraces the two instrument interface elements 411, 412. The second motor and lead screw arrangement 502 is attached to the drive interface element to the other side of where the drive interface element embraces the two instrument interface elements 411, 412.

Motor and lead screw arrangement 501 comprises a shaft 503 rigidly secured to arm 420 of drive interface element 418. The shaft 503 is parallel to the longitudinal axes 407 and 408 of the slideable units 403 and 404. The shaft is secured to a plate 504. Motor 506 drives a threaded screw 505 through a complimentary threaded aperture in the plate 504. When the motor drives the screw 505 in one direction, the plate moves in the direction 409. Thus, the part of the drive interface element 418 that the shaft 503 is secured to moves in the direction 409. When the motor drives the screw 505 in the opposing direction, the plate moves in the direction 410. Thus, the part of the drive interface element 418 that the shaft is secured to moves in the direction 410. The second motor and lead screw arrangement 502 works in the same manner.

The drive interface element 418 is moved from its position in FIG. 4*a* to its position in FIG. 4*b* by both motor and lead screw arrangements 501 and 502 driving the screws in the same direction, so as to cause the drive interface element 418, and hence the slideable units 403 and 404 to move in the direction 409.

The drive interface element 418 is moved from its position in FIG. 4*a* to its position in FIG. 4*c* by the motor and lead screw arrangements 501 and 502 driving their screws in opposing directions, such that the motor and lead screw arrangement 501 pushes the portion of the drive interface element 418 that it is connected to in the direction 410, and such that the motor and lead screw arrangement 502 pulls the portion of the drive interface element 418 that it is connected to in the direction 409, thereby causing the drive interface element 418 to rotate in a counter-clockwise direction about its axis 422.

FIG. 5 illustrates the motor and lead screw arrangements 501 and 502 as both being attached to the same arm 420 of drive interface element 418. However, any arrangement of the motor and lead screw arrangements 501 and 502 in which the whole of the drive interface element 418 can be linearly displaced and also rotated about its axis 422 may be used. For example, the motor and lead screw arrangements 501 and 502 may be attached to the other arm 421 of drive interface element 418. Or the motor and lead screw arrangements 501 and 502 may be attached to opposing ones of the arms 420 and 421.

Surgical drape 423 may be interposed between the robot arm and the surgical instrument so as to provide a barrier between the sterile instrument and the non-sterile robot arm. The surgical drape is located between the drive interface element 418 and the instrument interface elements.

Figure 6A:
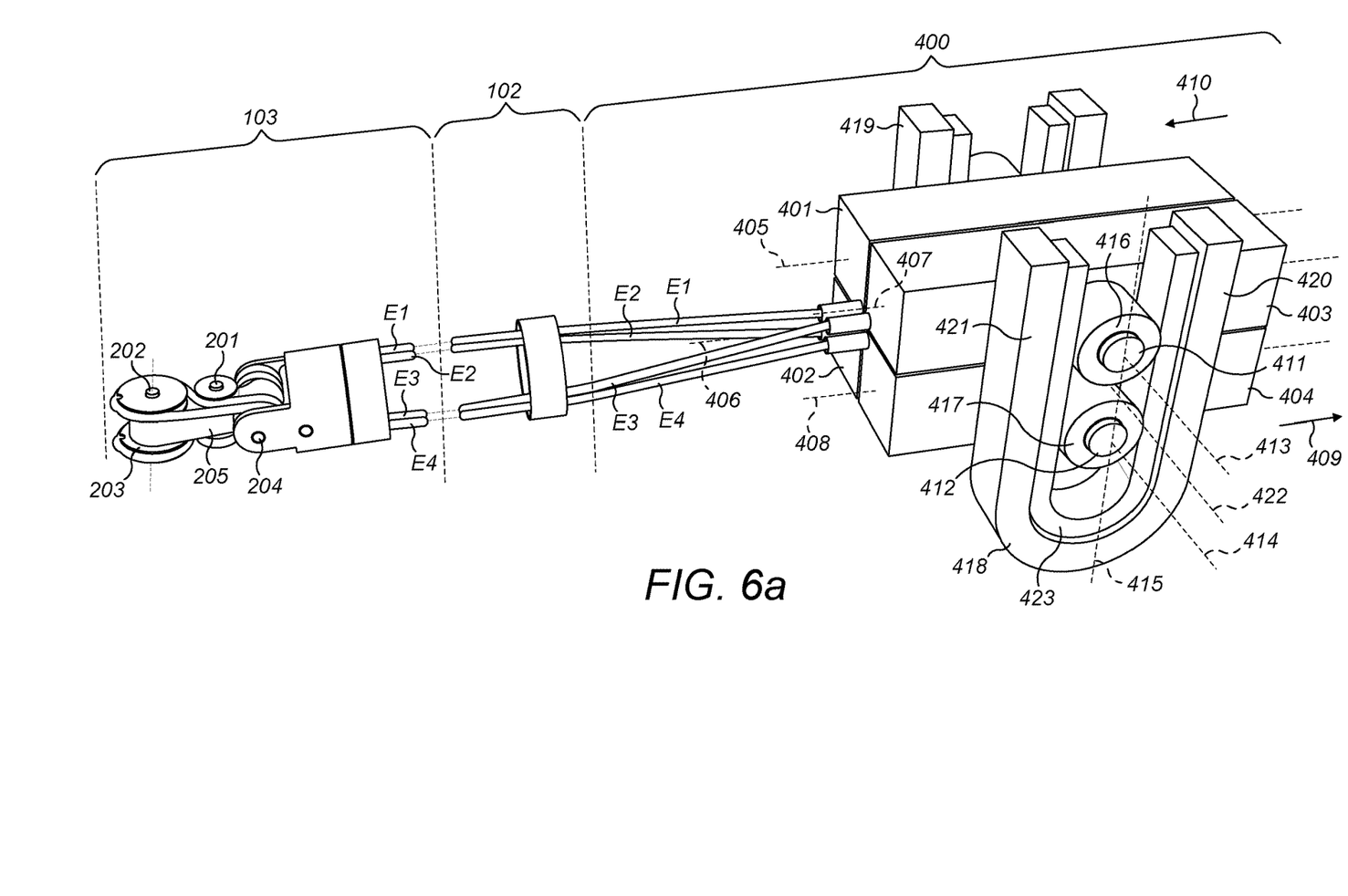
FIGS. 6a, 6b and 6c illustrate the components of FIGS. 4a, 4b and 4c as applied in an articulated surgical instrument.
Figure 6B:
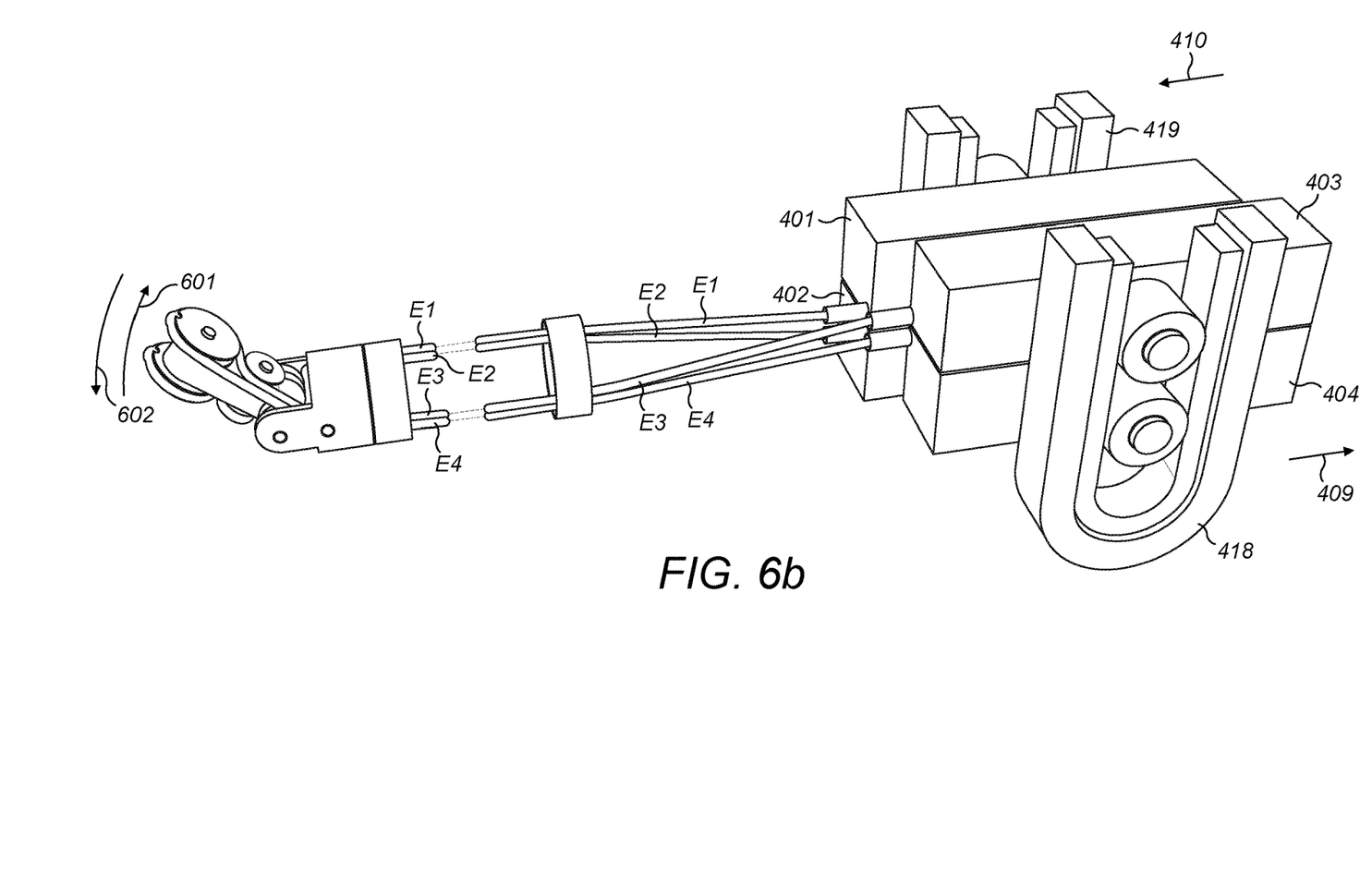
Figure 6C:
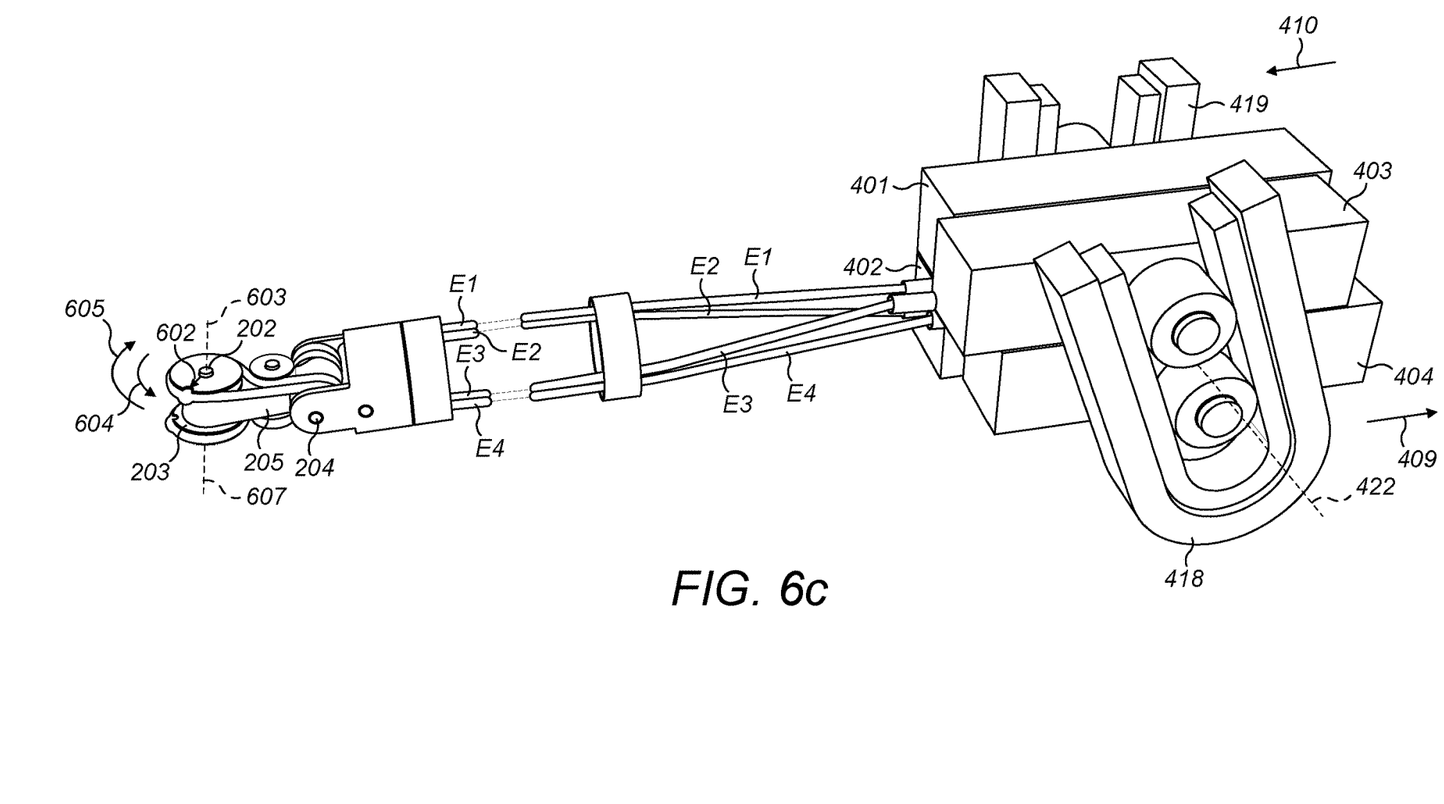

FIGS. 6a, 6b and 6c illustrate configurations in which the drive assembly and driving mechanism of FIGS. 4a, 4b and 4c is used to drive an articulation 103 at the distal end of the instrument shaft 102. Articulation 103 is as described with reference to FIG. 2. The articulation comprises a plurality of joints for articulating an end effector. The end effector comprises two opposing jaws. One of these jaws is rigidly attached to capstan 202. The other jaw of the end effector is rigidly attached to capstan 203. The joints of the articulation 103 are driven by the driving element pairs E1, E2 and E3, E4 of FIGS. 6a, 6b and 6c. Driving element pairs E1, E2 and E3, E4 engage the driving mechanism and drive assembly as described herein. Driving element pairs E1, E2, and E3, E4 extend through the hollow shaft 102 to the articulation 103 at the distal end of the shaft. Driving element pairs E1, E2 and E3, E4 engage with the articulation 103 at the distal end of the shaft as described with reference to FIG. 2, where E1 and E2 correspond to C3 and C4, and E3 and E4 correspond to C1 and C2.

The articulation is a wrist articulation, which includes pitch joint 204. Rotation about pitch joint 204 causes the wrist, and hence the end effector 104, to pitch relative to the shaft 102. FIG. 6b illustrates pitch joint 204 rotated relative to FIG. 6a in the direction marked 601. This is caused by tensioning driving element pair E3, E4 and de-tensioning or compressing driving element pair E1, E2. This is achieved by the drive assembly linearly displacing the drive interface element 418 in the direction 409 away from the articulation 301, and linearly displacing the drive interface element 419 in the direction 410 towards the articulation 301. Suitably, the drive assembly linearly displaces the drive interface element 418 away from the distal end of the shaft, and linearly displaces the drive interface element 419 towards the distal end of the shaft. Conversely, pitch joint 204 is caused to rotate in the opposing direction marked 602 on FIG. 6b by tensioning driving element pair E1, E2 and de-tensioning or compressing driving element pair E3, E4. This is achieved by the drive assembly linearly displacing the drive interface element 418 in the direction 410 towards the articulation 301, and linearly displacing the drive interface element 419 in the direction 409 away from the articulation 301. Suitably, the drive assembly linearly displaces the drive interface element 418 towards the distal end of the shaft, and linearly displaces the drive interface element 419 away from the distal end of the shaft.

Rotation about capstan 202 causes a first jaw of the end effector to rotate about the central axis 603 of capstan 202. FIG. 6c illustrates a rotation of the capstan 202 in the direction 604 such that the first jaw is pointing in the direction indicated by arrow 606. The first jaw is caused to rotate in the direction marked 604 by tensioning driving element E4 and de-tensioning or compressing driving element E3. This is achieved by drive assembly rotating drive interface element 418 about its axis 422 in an anticlockwise direction. In other words, the base of the U-shaped element 418 moves away from the articulation, and the top of the U-shaped element moves towards the articulation. Conversely, the first jaw is caused to rotate in the opposing direction marked 605 by tensioning driving element E3 and de-tensioning or compressing driving element E4. This is achieved by drive assembly rotating drive interface element 418 about its axis 422 in a clockwise direction. In other words, the base of the U-shaped element 418 moves towards the articulation, and the base of the U-shaped element moves away from the articulation. The tension status of driving elements E1 and E2 are immaterial to driving rotation of the first jaw about capstan 202. The motions of driving element pair E1, E2 and driving element pair E3, E4 are not coupled when driving rotation about capstan 202.

Rotation about capstan 203 causes a second jaw of the end effector to rotate about the central axis 607 of capstan 203. Central axis 607 of capstan 203 is parallel to central axis 603 of capstan 202. Suitably, central axis 607 of capstan 203 is collinear with central axis 603 of capstan 202. The second jaw is caused to rotate in the direction marked 604 by tensioning driving element E2 and de-tensioning or compressing driving element E1. This is achieved by drive assembly rotating drive interface element 419 about its axis in an anticlockwise direction. In other words, the base of the U-shaped element 419 moves away from the articulation, and the top of the U-shaped element moves towards the articulation. Conversely, the second jaw is caused to rotate in the opposing direction marked 605 by tensioning driving element E1 and de-tensioning or compressing driving element E2. This is achieved by drive assembly rotating drive interface element 419 about its axis in a clockwise direction. In other words, the base of the U-shaped element 419 moves towards the articulation, and the base of the U-shaped element moves away from the articulation. The tension status of driving elements E3 and E4 are immaterial to driving rotation of the second jaw about capstan 203. The motions of driving element pair E1, E2 and driving element pair E3, E4 are not coupled when driving rotation about capstan 203.

The driving mechanism independently drives motion of pitch joint 204 and each of the jaws by capstans 202 and 203. One or both jaws may be actuated concurrently with pitching the wrist by driving the driving elements E1, E2, E3 and E4 as described above.

The driving elements E1, E2, E3 and E4 are flexible. Each driving element is elongate. Each driving element can be flexed laterally to its main extent. In other words, each driving element can be flexed transversely to its longitudinal axis. Each driving element is not flexible along its main extent. Each driving element resists compression and tension forces acting in the direction of its longitudinal axis. Thus, the driving elements are able to transfer drive from the proximal end of the instrument to the articulation. The driving elements may be cables.

Each driving element illustrated in FIGS. 6a, 6b and 6c is rigidly secured to the capstan about which it terminates in the articulation. In FIGS. 6a, 6b and 6c, driving element pair E1, E2 is rigidly fixed to capstan 202 at the point on capstan 202 which is most distal to the driving mechanism 400 and lies on the longitudinal axis of the shaft when the end effector, articulation and shaft are in the straight configuration shown in FIG. 6a. Similarly, in FIGS. 6a, 6b and 6c, driving element pair E3, E4 is rigidly fixed to capstan 203 at the point on capstan 203 which is most distal to the driving mechanism 400 and lies on the longitudinal axis of the shaft when the end effector, articulation and shaft are in the straight configuration shown in FIG. 6a.

In an alternative configuration, driving elements E1 and E2 may be disconnected at the articulation. In other words, driving elements E1 and E2 may not form a continuous element about the capstan 203. Instead, driving elements E1 and E2 may each individually terminate at capstan 203, to which they are individually secured. Similarly, driving elements E3 and E4 may be disconnected at the articulation. In other words, driving elements E3 and E4 may not form a continuous element about the capstan 202. Instead, driving elements E3 and E4 may each individually terminate at capstan 202, to which they are individually secured.

Suitably, the longitudinal axis of the distal end of the robot arm is collinear with the longitudinal axis of the shaft of the instrument. And the longitudinal axes of the slideable units are parallel to the longitudinal axes of the distal end of the robot arm and the instrument shaft.

It may be desirable for the driving mechanism to be located in a different orientation or location at the proximal end of the instrument shaft in order to utilise the space in the central interior area of the instrument shaft for other components. In this case, additional pulleys may be used compared to FIGS. 4a, 4b and 4c to locate the driving mechanism in the alternative orientation/location. This alternative orientation/location may be such that the longitudinal axes of the slideable units are no longer parallel to the longitudinal axis of the instrument shaft. The drive assembly displaces the drive interface elements 418, 419 linearly to the longitudinal axes of the slideable units. However, this linear movement may no longer be parallel to the longitudinal axis of the instrument shaft. However, by means of the additional pulleys, the same motions of the driving elements in the shaft are achieved by driving the drive interface elements 418, 419.

FIGS. 6a, 6b and 6c illustrate the driving mechanism of FIGS. 4a, 4b and 4c driving an articulation 103 at the distal end of the instrument shaft 102. The driving mechanism of FIGS. 4a, 4b and 4c may be used to drive other configurations of articulation at the distal end of an instrument shaft. The driving mechanism of FIGS. 4a, 4b and 4c can drive any articulation which is driveable with two pairs of driving elements which are capable of transferring motion as described herein.

It will be appreciated that the drive assembly and the driving mechanisms described herein could be modified to include further driving elements to transfer drive to further joints of an articulation at the distal end of the instrument shaft.

The driving mechanism described herein de-tensions the driving elements E1, E2, E3 and E4 completely when the joint is in the straight configuration shown in FIG. 4a.

In the interfacing arrangement described herein, the robot arm interfaces directly with the surgical instrument without using an intermediate interface plate. The driving mechanism slots easily into the two U-shaped drive interface elements.

Suitably, the slideable units are fabricated from nylon. Suitably, the drive interface elements are aluminium. Suitably, the drape is fabricated from polyester, polypropylene, polyethylene or polytetrafluoroethylene.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument comprising:
    a shaft;
    a first driving element and a second driving element;
    an articulation attached to a distal end of the shaft, the articulation configured to articulate an end effector, the articulation drivable by at least the first driving element and the second driving element; and
    a driving mechanism at a proximal end of the shaft, the driving mechanism comprising:
        a first slidable unit to which the first driving element is secured, and a second slidable unit to which the second driving element is secured, wherein the first and second slidable units are permitted to slide linearly relative to each other; and
        a first instrument interface element connected to the first slidable unit, and a second instrument interface element connected to the second slidable unit, both the first and second instrument interface elements being drivable in a same linear direction so as to drive both the first and second driving elements in the same direction, and the first and second instrument interface elements are drivable in opposing linear directions so as to drive the first and second driving elements in opposing directions.

2. The robotic surgical instrument as claimed in claim 1, wherein the first and second slidable units are stacked such that longitudinal axes of the first and second slidable units are parallel, and the first and second slidable units are permitted to slide parallel to their longitudinal axes.

3. The robotic surgical instrument as claimed in claim 1, wherein the first instrument interface element is a first rod protruding from the first slidable unit in a direction transverse to a longitudinal axis of the first slidable unit, and the second instrument interface element is a second rod protruding from the second slidable unit in a direction transverse to a longitudinal axis of the second slidable unit.

4. The robotic surgical instrument as claimed in claim 3, wherein in a configuration in which the articulation is de-tensioned, the first and second rods are aligned along an axis transverse to the longitudinal axes of the first and second slidable units and transverse to the longitudinal axes of the first and second rods.

5. The robotic surgical instrument as claimed in claim 3, wherein the first and second rods are each encompassed in a foam roller.

6. The robotic surgical instrument as claimed in claim 1, wherein the articulation is additionally drivable by a third driving element and a fourth driving element; and wherein the driving mechanism further comprises:
    a third slidable unit to which the third driving element is secured, and a fourth slidable unit to which the fourth driving element is secured, wherein the first, second, third and fourth slidable units are permitted to slide linearly relative to each other; and
    a third instrument interface element connected to the third slidable unit, and a fourth instrument interface element connected to the fourth slidable unit, the third and fourth instrument interface elements being drivable in a same linear direction so as to drive both the third and fourth driving elements in the same direction, and the third and fourth instrument interface elements are drivable in opposing linear directions so as to drive the third and fourth driving instrument interface elements in opposing directions.

7. The robotic surgical instrument as claimed in claim 6, wherein the first, second, third and fourth slidable units are stacked in a 2x2 configuration, such that the first and second instrument interface elements are on an opposing face of the 2x2 configuration from the third and fourth instrument interface elements.

8. The robotic surgical instrument as claimed in claim 6, wherein the articulation is a wrist articulation comprising a pitch joint which is configured to pitch the wrist articulation, the first, second, third and fourth driving elements being connected to the wrist articulation such that:
   (i) when the first and second slidable units are displaced linearly in a first direction, and the third and fourth slidable units are displaced linearly in the opposing direction, the wrist articulation pitches in one direction about the pitch joint; and
   (ii) when the first and second slidable units are displaced linearly in the opposing direction, and the third and fourth slidable units are displaced linearly in the first direction, the wrist articulation pitches in the opposing direction about the pitch joint.

9. The robotic surgical instrument as claimed in claim 6, wherein the articulation comprises a joint configured to actuate opposing first and second jaws of an end effector, the third and fourth driving elements are connected to the joint such that when the third and fourth slidable units are displaced linearly in opposing directions away from each other, the second jaw rotates in one direction about the joint, and when the third and fourth slidable units are displaced linearly in opposing directions towards each other, the second jaw rotates in an opposing direction about that joint.

10. The robotic surgical instrument as claimed in claim 6, wherein the third and fourth instrument interface elements are configured to engage with a second drive interface element of a drive assembly.

11. The robotic surgical instrument as claimed in claim 1, wherein the articulation comprises a joint configured to actuate opposing first and second jaws of an end effector, the first and second driving elements being connected to the joint such that when the first and second slidable units are displaced linearly in opposing directions away from each other, the first jaw rotates in one direction about the joint, and when the first and second slidable units are displaced linearly in opposing directions towards each other the first jaw rotates in an opposing direction about that joint.

12. The robotic surgical instrument as claimed in claim 1, wherein the first and second instrument interface elements are configured to engage with a first drive interface element of a drive assembly.

* * * * *

UNITED STATES PATENT AND TRADEMARK OFFICE
CERTIFICATE OF CORRECTION

| | |
|---|---|
| PATENT NO. | : 11,684,436 B2 |
| APPLICATION NO. | : 16/909012 |
| DATED | : June 27, 2023 |
| INVENTOR(S) | : Keith Marshall and Steven James Randle |

It is certified that error appears in the above-identified patent and that said Letters Patent is hereby corrected as shown below:

In the Claims

Column 13, Line 2, In Claim 6, delete the text "instrument interface".

Signed and Sealed this
First Day of August, 2023

Katherine Kelly Vidal
Director of the United States Patent and Trademark Office